(12) United States Patent
Olson et al.

(10) Patent No.: US 7,988,027 B2
(45) Date of Patent: Aug. 2, 2011

(54) CRIMP AND RELEASE OF SUTURE HOLDING BUTTRESS MATERIAL

(75) Inventors: Lee Olson, Wallingford, CT (US); Ernie Aranyi, Easton, CT (US); Patrick Mozdzierz, Rocky Hill, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 177 days.

(21) Appl. No.: 12/540,483

(22) Filed: Aug. 13, 2009

(65) Prior Publication Data
US 2010/0249805 A1 Sep. 30, 2010

Related U.S. Application Data

(63) Continuation-in-part of application No. 12/414,943, filed on Mar. 31, 2009, and a continuation-in-part of application No. 12/414,931, filed on Mar. 31, 2009, and a continuation-in-part of application No. 12/414,961, filed on Mar. 31, 2009.

(51) Int. Cl.
*A61B 17/068* (2006.01)

(52) U.S. Cl. .............. 227/175.1; 227/176.1; 227/181.1; 606/151; 606/219; 606/139

(58) Field of Classification Search ............... 227/175.1, 227/176.1, 181.1; 606/151, 219, 139
See application file for complete search history.

(56) References Cited

U.S. PATENT DOCUMENTS

| | | | |
|---|---|---|---|
| 3,054,406 A | 9/1962 | Usher | |
| 3,124,136 A | 3/1964 | Usher | |
| 4,347,847 A | 9/1982 | Usher | |
| 4,354,628 A | 10/1982 | Green | |
| 4,452,245 A | 6/1984 | Usher | |
| 4,605,730 A | 8/1986 | Shalaby et al. | |
| 4,655,221 A | 4/1987 | Devereux | |
| 4,834,090 A | 5/1989 | Moore | |
| 4,838,884 A | 6/1989 | Dumican et al. | |
| 4,930,674 A | 6/1990 | Barak | |
| 5,002,551 A | 3/1991 | Linsky et al. | |
| 5,014,899 A | 5/1991 | Presty et al. | |
| 5,040,715 A | 8/1991 | Green et al. | |
| 5,065,929 A | 11/1991 | Schulze et al. | |
| 5,205,459 A | 4/1993 | Brinkerhoff et al. | |

(Continued)

FOREIGN PATENT DOCUMENTS

DE 1 99 24 311 11/2000
(Continued)

OTHER PUBLICATIONS

European Search Report for corresponding EP 10 25 1437 application, date of completion is Nov. 22, 2010 (3 pages).

(Continued)

*Primary Examiner* — Rinaldi I. Rada
*Assistant Examiner* — Michelle Lopez (57) ABSTRACT

A mechanism is provided for crimping and releasing a suture securing a strip of buttress material to an end effector. The mechanism includes a retention member movably mounted within the end effector. The retention member is movable from a first position crimping the suture to the end effector to a second position releasing the suture from the end effector. The mechanism additionally includes a follower member, engageable with the retention member, and movable in response to actuation of a surgical instrument to move the retention member between the first and second positions. A lock mechanism is also provided to secure the retention member in the first position. The follower member operates to disengage the lock mechanism.

19 Claims, 5 Drawing Sheets

U.S. PATENT DOCUMENTS

| | | |
|---|---|---|
| 5,263,629 A | 11/1993 | Trumbull et al. |
| 5,314,471 A | 5/1994 | Brauker et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,319,264 B1 | 11/2001 | Tormala et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,704,210 B1 | 3/2004 | Myers |
| 6,712,853 B2 | 3/2004 | Kuslich |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,927,315 B1 | 8/2005 | Heinecke et al. |
| 7,128,748 B2 | 10/2006 | Mooradian et al. |
| 7,147,138 B2 * | 12/2006 | Shelton, IV ................ 227/176.1 |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,604,151 B2 | 10/2009 | Hess et al. |
| 7,665,646 B2 | 2/2010 | Prommersberger |
| 7,744,627 B2 | 6/2010 | Orban, III et al. |
| 7,793,813 B2 | 9/2010 | Bettuchi |
| 7,823,592 B2 | 11/2010 | Bettuchi et al. |
| 7,845,533 B2 | 12/2010 | Marczyk et al. |
| 7,845,536 B2 | 12/2010 | Viola et al. |
| 2002/0016626 A1 | 2/2002 | DiMatteo et al. |
| 2002/0019187 A1 | 2/2002 | Carroll et al. |
| 2002/0035401 A1 | 3/2002 | Boyce et al. |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2002/0177859 A1 | 11/2002 | Monassevitch et al. |
| 2003/0009181 A1 | 1/2003 | Gellman et al. |
| 2003/0065345 A1 | 4/2003 | Weadock |
| 2003/0065346 A1 | 4/2003 | Evens et al. |
| 2003/0083676 A1 | 5/2003 | Wallace |
| 2003/0088256 A1 | 5/2003 | Conston et al. |
| 2003/0105510 A1 | 6/2003 | DiMatteo et al. |
| 2003/0114866 A1 | 6/2003 | Ulmsten et al. |
| 2003/0120284 A1 | 6/2003 | Palacios |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2003/0212460 A1 | 11/2003 | Darois et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0228446 A1 | 10/2005 | Mooradian et al. |
| 2005/0245965 A1 | 11/2005 | Orban et al. |
| 2006/0004407 A1 | 1/2006 | Hiles et al. |
| 2006/0085034 A1 | 4/2006 | Bettuchi |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0212050 A1 | 9/2006 | D'Agostino et al. |
| 2006/0271104 A1 | 11/2006 | Viola et al. |
| 2007/0034669 A1 | 2/2007 | de la Torre et al. |
| 2007/0049953 A2 | 3/2007 | Shimoji et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |

| | | |
|---|---|---|
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0078739 A1 | 3/2009 | Viola |
| 2009/0095791 A1 | 4/2009 | Bauman et al. |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277947 A1 | 11/2009 | Viola |

FOREIGN PATENT DOCUMENTS

| | | |
|---|---|---|
| EP | 0 327 022 | 8/1989 |
| EP | 0 594 148 | 4/1994 |
| EP | 1 520 525 | 4/2005 |
| EP | 2 005 895 A2 | 12/2008 |
| WO | WO 90/05489 | 5/1990 |
| WO | WO 98/17180 | 4/1998 |
| WO | WO 99/45849 | 9/1999 |
| WO | WO 03/082126 A1 | 10/2003 |
| WO | WO 03/105698 A2 | 12/2003 |
| WO | WO 2006/023578 | 3/2006 |
| WO | WO 2006/044490 | 4/2006 |
| WO | WO 2006/083748 | 8/2006 |
| WO | WO 2008/109125 A1 | 9/2008 |

OTHER PUBLICATIONS

International Search Report from Application No. EP 06016962.0 dated Jan. 3, 2007.
International Search Report from Application No. PCT/US05/36740 mailed Mar. 23, 2007.
International Search Report from Application No. PCT/US2008/002981 dated Jun. 26, 2008.
European Search Report from Application No. EP 08 25 1779 dated Jul. 23, 2008.
European Search Report from Application No. EP 06 000 4598 dated Jun. 22, 2006.

* cited by examiner

CRIMP AND RELEASE OF SUTURE HOLDING BUTTRESS MATERIAL

CROSS-REFERENCE TO RELATED APPLICATIONS

The present application is a Continuation-in-Part Application claiming the benefit of and priority to U.S. patent application Ser. No. 12/414,943, filed on Mar. 31, 2009, the entire content of which is incorporated herein by reference.

The present application is a Continuation-in-Part Application claiming the benefit of and priority to U.S. patent application Ser. No. 12/414,931, filed on Mar. 31, 2009, the entire content of which is incorporated herein by reference.

The present application is a Continuation-in-Part Application claiming the benefit of and priority to U.S. patent application Ser. No. 12/414,961, filed on Mar. 31, 2009, the entire content of which is incorporated herein by reference.

BACKGROUND

1. Technical Field

The present disclosure relates to a system of attaching and releasing buttress material from an anvil. More particularly, the present disclosure relates to a retention and release mechanism for crimping and disengaging a buttress material retention suture from the anvil.

2. Background of Related Art

During various surgical procedures it is often necessary to reattach two sides of tissue. This is typically accomplished by approximating two edges of the tissues flush against one another and securing them by stapling, suturing, etc. In some instances, the staple or suture line connecting the tissues may tear or pull through the tissues, particularly, where the tissues are relatively weak. Additionally, during healing, leakage may occur through the staple or suture lines.

In order to alleviate these problems, a strip of material, called "buttress material" is positioned against the tissues prior to stapling or suturing. The buttress material tends to reinforce the staple or suture line as well as cover the juncture of the tissues to prevent leakage prior to healing.

In certain minimally invasive surgical procedures the buttress material may be pre-attached to the surgical instrument being used. For example, the buttress material can be attached to a staple cartridge or anvil assembly of a surgical stapling instrument. The buttress material is retained by various means such as, for example, adhesives, etc.

Therefore, it is desirable to provide a cartridge or an anvil assembly incorporating a suture retention and release mechanism which allows for easy assembly, easy retention, and/or subsequent release of a buttress material retention suture after tissues have been stapled.

SUMMARY

There is disclosed a surgical instrument generally including a handle member having a movable part or trigger mounted to the handle member and an elongate tubular member extending distally from the handle member. An end effector assembly is mounted on a distal end of the elongate tubular member. The end effector assembly includes a first member having an under side and a top side, the underside having a face. A strip of buttress material is positioned against the face of the first member. A retention component is provided having a backspan and first and second ends extending from the backspan. The backspan is positioned across the strip of buttress material and the first end extends from the underside to the top side of the first member.

The top side of the first member, in certain embodiments, includes a head and a pocket located proximal to the head. The retention member may be movably mounted in the pocket and the first end of the retention component can be releasably secured between a proximal face of the head and the distal face of the retention member. The retention member includes a push plate in certain embodiments, the push plate having a distal face, and the first end of the retention component is releasably secured between the distal face of the push plate and the proximal face of the head.

In one embodiment, the first member includes a clearance track such that the first end of the retention component passes from the underside of the first member to the top side of the first member through the clearance track. In a specific embodiment, the clearance track passes through the pocket.

The first member desirably further includes a pair of side walls defining a channel, each sidewall having a distal face. The retention member may include a tab movable between the channel and the pocket such that a proximal face of the tab engages a distal face of the sidewall when the tab is in the pocket.

The retention member, in certain embodiments, includes a flexible leg and the tab is located on a distal end of the flexible leg. The flexible leg is in a constrained condition when in the channel and in an expanded condition when the tab is distal of the distal face of the side wall. The retention member further includes a bar extending from the push plate to a proximal end of the flexible leg such that the tab is within the channel in a proximal position and in engagement with the distal face of the side wall in a distal position to lock the push plate into engagement with the first end of the retention component.

The retention and release mechanism may further include a follower movable within the channel. The follower is engageable with the flexible leg to move the flexible leg between the constrained and expanded conditions.

In one embodiment, the retention member includes a second flexible leg affixed to the proximal end of the bar. The second flexible leg also includes a tab engageable with one of the distal faces of the sidewalls.

In another embodiment, the first member has a second clearance track such that the second end of the retention component passes from the underside of the first member to the top side of the first member through the second clearance track.

In a specific embodiment, the strip of buttress material includes first and second cutouts for passage of the first and second ends of the retention component.

A retention member is movably mounted on the top side of the first member such that the first end of the retention component is releasably secured between a distal face of the retention member and a proximal face of the first member. The retention component can include a laterally movable tab for engaging the first member.

In certain embodiments, the movable part or trigger of the surgical instrument is operable to move the retention member from a first position securing the first and second ends of the retention component between a distal face of the retention member and a proximal face of the first member to a second position allowing the retention member to move away from the first and second ends of the retention component.

In certain embodiments, the first member is an anvil member and the instrument includes a surgical stapling cartridge. The retention member may have a locked position, securing the retention component. The retention member has at least one tab for maintaining the retention member in the locked position. The at least one tab may be laterally movable to engage the anvil member. In certain embodiments, the instrument includes a follower for moving the at least one tab, allowing movement of the retention member away from the locked position.

DESCRIPTION OF THE DRAWINGS

An embodiment of the presently disclosed suture retention and release mechanism for use with a buttressed anvil assembly is disclosed herein with reference to the drawings, wherein.

DETAILED DESCRIPTION OF EMBODIMENTS

An embodiment of the presently disclosed retention and release mechanism for use in a buttressed anvil assembly will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
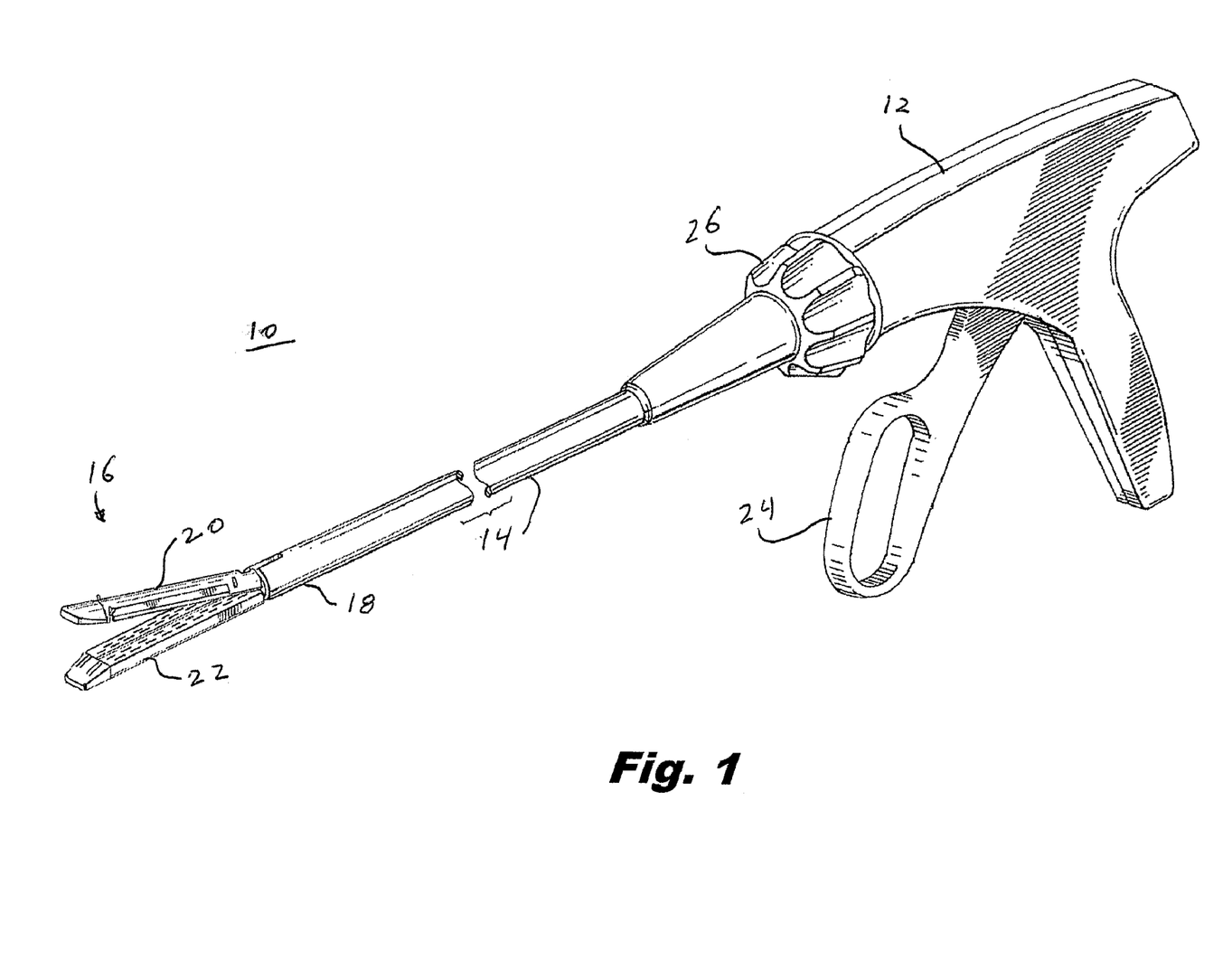
FIG. 1 is a perspective view of a surgical stapling instrument having a buttressed anvil assembly incorporating a suture retention and release mechanism.

Referring to FIGS. 1-9, and initially with regard to FIG. 1, there is illustrated a surgical stapling instrument 10 incorporating an embodiment of the presently disclosed suture retention and release mechanism. Surgical stapling instrument 10 generally includes a pistol grip style handle 12 having an elongate tubular member 14 extending distally from handle 12. An end effector assembly 16 extends distally from a distal end 18 of elongate tubular member 14. End effector assembly 16 has a pair of end effectors including a buttressed anvil assembly 20 and a staple cartridge 22. Buttressed anvil assembly 20 is movably mounted relative to staple cartridge 22 and is movable from an open position spaced apart from staple cartridge 22 to a closed position bringing buttressed anvil assembly 20 into close cooperative alignment with staple cartridge 22. A movable part or trigger 24 is provided on handle 12 and is operable to move buttressed anvil assembly 20 between the open and closed positions. Additionally, trigger 24 is operable to actuate staple cartridge 22 in order to eject staples (not shown) contained in staple cartridge 22 from staple cartridge 22 into staple crimping pockets (FIG. 3) on buttressed anvil assembly 20 in a manner described in more detail herein below. A rotation knob 26 is provided on handle 12 to rotate elongate tubular member 16 and thereby orient end effector assembly 16 relative to a tissue being operated upon.

Figure 2:
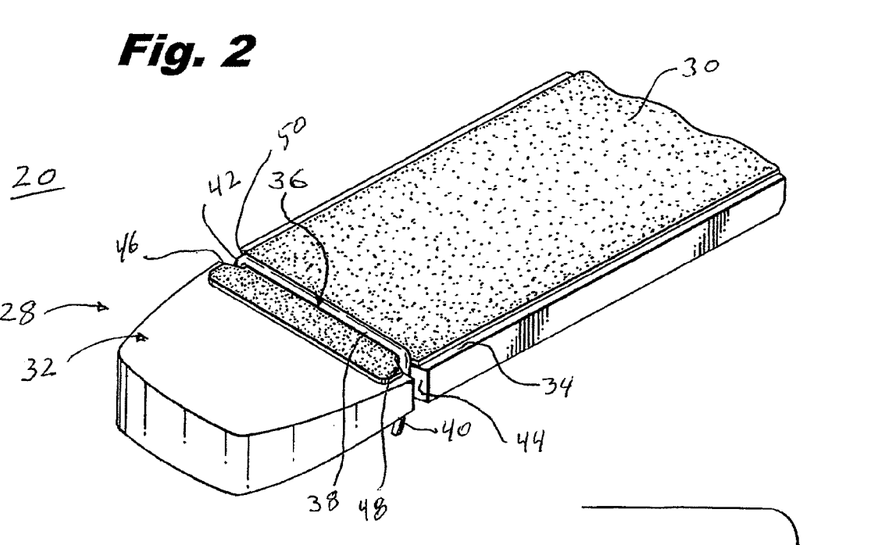
FIG. 2 is a perspective view, taken from below, of a distal end of the buttressed anvil assembly including a strip of buttress material and a retention suture.
Figure 3:
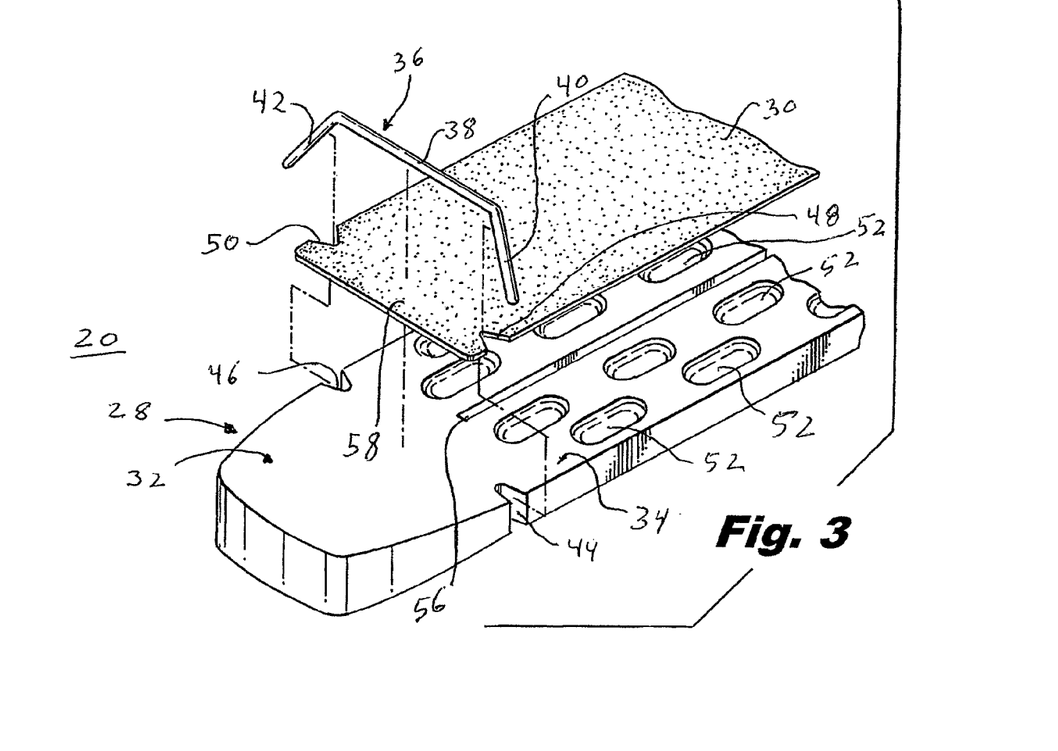
FIG. 3 is a perspective view of the distal end of the buttressed anvil assembly similar to FIG. 2 with parts separated.

Referring now to FIGS. 2 and 3, buttressed anvil assembly 20 generally includes an anvil member 28 having a strip of buttress material 30 positioned on an underside 32 of anvil member 28. Specifically, strip of buttress material 30 is positioned to lie on an anvil face 34 of anvil member 28. A retention component 36 is provided to maintain and secure strip of buttress material 30 in contact with anvil face 34 of anvil member 28 prior to stapling of tissue. Retention component 36 can comprise a strap, a suture, a thread, a cable, etc., and includes a backspan 38 and first and second ends 40 and 42, respectively, extending from backspan 38. Backspan 38 engages strip of buttress material 30 to hold strip of buttress material 30 against anvil face 34. First end 40 and second end 42 pass through clearance tracks such as first and second clearance tracks 44 and 46 formed in anvil member 28 and are secured to anvil member 28 in a manner described in more detail herein below. It should be noted that first and second clearance tracks 44 and 46, respectively, are dimensioned to allow first end 40 and second end 42 of retention component 36 to pass freely there through without binding or cinching within first clearance track 44 and second clearance track 46. Alternatively, one of first and second ends 40 and 42 of retention component 36 may be cinched or otherwise attached to anvil member 28 to retain retention component 36 with anvil member 28 upon removal of the operative site. Retention component 36 can be flexible, resilient, or rigid. Retention component 36 can be separate from, or integrally formed with the buttress material 30.

Strip of buttress material 30 includes first and second cutouts 48 and 50 for passage of first and second ends 40 and 42 of retention component 36 to prevent bunching or rolling of strip of buttress material 30. Strip of buttress material 30 and retention component 36 are formed of any commonly know materials used for buttress materials and sutures generally, including absorbable, resorbable materials, etc.

Referring for the moment to FIG. 3, anvil face 34 of anvil member 28 is provided with a plurality of staple clinching pockets 52 which serve to receive and clinch free ends of staples (not shown) ejected from staple cartridge 22 (FIG. 1) in a manner commonly known in stapling instruments. Additionally, a knife slot 54 extends completely through a substantial portion of anvil member 28 to accommodate passage of a knife blade (not shown) to sever tissue as well as sever strip of buttress material 30 down its length. When strip of buttress material 30 extends distally beyond a distal end 56 of knife slot 54, it is contemplated that a distal end 58 of strip of buttress material 30 will be perforated, slotted or otherwise constructed to allow strip of buttress material 30 to be separated into two halves in line with that portion cut by the knife blade.

Figure 4:
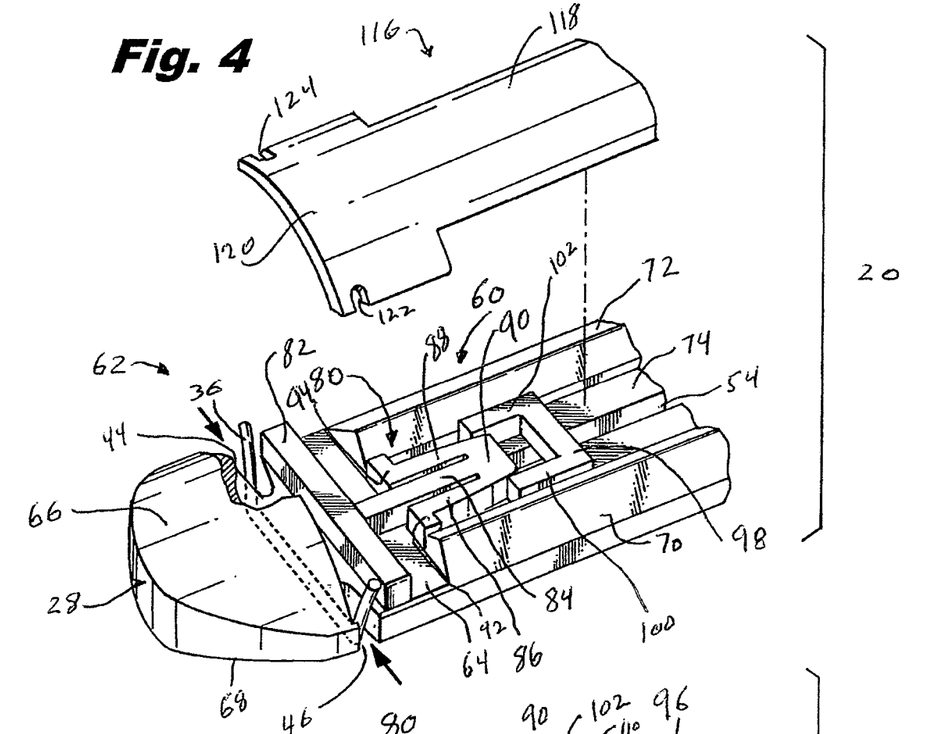
FIG. 4 is a perspective view, taken from above, of the distal end of the buttressed anvil assembly with an anvil cover removed.
Figure 5:
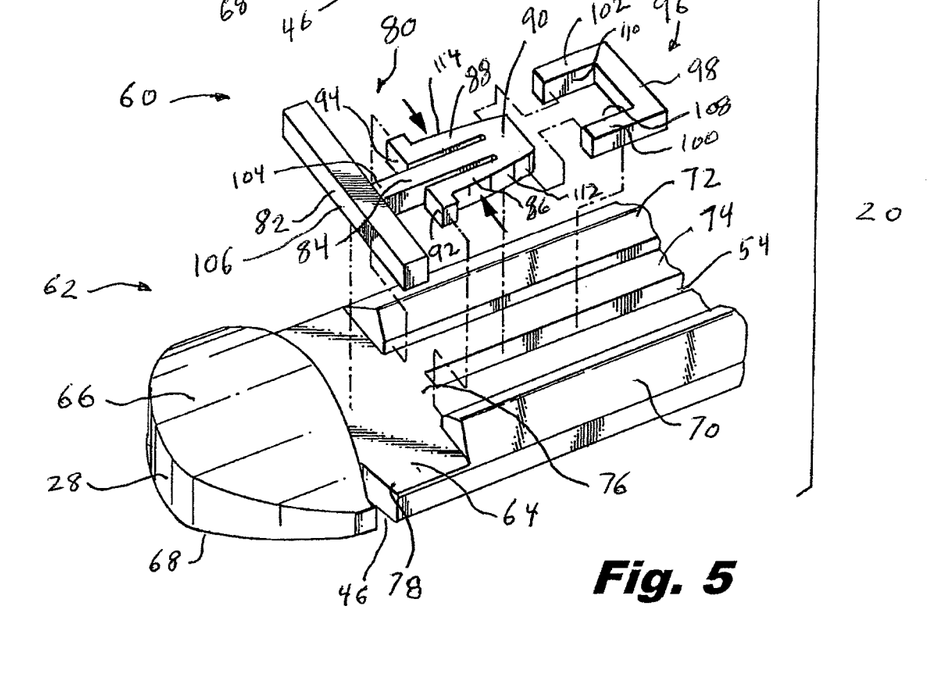
FIG. 5 is a perspective view, similar to FIG. 4, with parts separated.

Referring now to FIGS. 4 and 5, and as noted above, buttressed anvil assembly 20 is provided with a retention and release mechanism 60 to secure and release retention component or suture 36 (FIG. 2) from engagement with anvil member 28. A top side 62 of anvil member 28 includes a pocket 64 formed between an head 66, formed in a distal end 68 of anvil member 28, and a pair of side walls 70 and 72, respectively, located proximal to pocket 64. Side walls 70 and 72 define a channel 74 therebetween. Knife slot 54 extends through channel 74 to a proximal end 76 of pocket 64 (FIG. 5). As shown, clearance tracks 44 and 46 pass through a distal end 78 of pocket 64.

Retention and release mechanism 60 includes a retention member 80 positioned within pocket 64 and channel 74. Retention member 80 is provided to secure first and second ends 40 and 42 of retention component 36 against head 66. Retention member 80 includes a rectangular push plate 82 positioned within pocket 64 and oriented perpendicular to a long axis of anvil member 28. A bar 84 extends proximally from push plate 82 and extends into channel 74. A pair of flexible arms 86 and 88 extend distally from an enlarged proximal end 90 of bar 84. Flexible arms 86 and 88 assist in securing push plate 82 distally within pocket 64 and against retention component 36. A pair of tabs 92 and 94 extend outwardly from flexible arms 86 and 88, respectively, and are provided to engage respective side walls 70 and 72 when push plate is in a distal position within pocket 64.

Retention member 80 may be formed from a variety of materials such as, for example, plastics, shape memory materials or alloys or other such materials which would allow arms 86 and 88 to flex while maintaining sufficient rigidity to push plate 82 to secure retention component 36 against head 66.

Retention and release mechanism 60 further includes a follower 96 positioned proximally within channel 74 relative to retention member 80. In the embodiment shown, follower 96 is U-shaped and includes a base 98 and legs 100 and 102 extending distally from base 98. Legs 100 and 102 are provided to engage and squeeze flexible arms 86 and 88 of retention member 80 in order to assist in releasing tabs 92 and 94 from engagement with side walls 70 and 72. This allows push plate 82 to disengage from retention component 36 in a manner described in more detail below. U-shaped follower 96 may be formed of a variety of relatively rigid materials such as, for example, plastics, stainless steels, etc. so as to have sufficient strength to compress flexible arms 86 and 88 retention member 80.

Referring specifically for the moment to FIG. 5, a distal end 104 of bar 84 extends from a center 106 of push plate 82. Inner surfaces 108 and 110 of legs 100 and 102 engage respective outer surfaces 112 and 114 of flexible arms 86 and 88 to collapse or force them inwardly toward bar 84.

With reference back to FIG. 4, in order to maintain retention member 80 and U-shaped follower 96 within anvil member 28, buttressed anvil assembly 20 further includes a cover 116 having a longitudinal proximal end 118 which overlies channel 74 in anvil member 28. An enlarged rectangular distal end 120 of cover 116 fits into pocket 64, over retention member 80, and may be snap fit, welded, glued, etc. Cutouts 122 and 124 are provided in enlarged rectangular distal end 120 to allow passage of first and second ends 40 and 42 of retention component 36 in order to trim any excess suture material flush with cover 116.

Now, with reference to FIGS. 2-3 and 6-9, and initially with regard to FIG. 6, the assembly and use of buttressed anvil assembly 20 will now be described. In the preassembled condition, a portion of retention member 80 is in a proximal position within channel 74. Specifically, tabs 92 and 94 are located within channel 74 causing flexible arms 86 and 88 to be in a stressed or constrained condition within channel 74. Follower 96 is also in a proximal position within channel 74.

Referring for the moment to FIG. 3, initially, strip of buttress material 30 is placed over anvil face 34 of anvil member 28. Retention component 36 is positioned over strip of buttress material 30 such that backspan 38 of retention component 36 engages strip of buttress material 30 to hold strip of buttress material 30 against anvil face 34 (see FIG. 2). As noted herein above, strip of buttress material 30 is provided with cutouts 48 and 50 to receive first and second ends 40 and 42, respectively, of retention component 36 in order to prevent bunching or wrinkling of strip of buttress material 30.

Figures 6, 7:
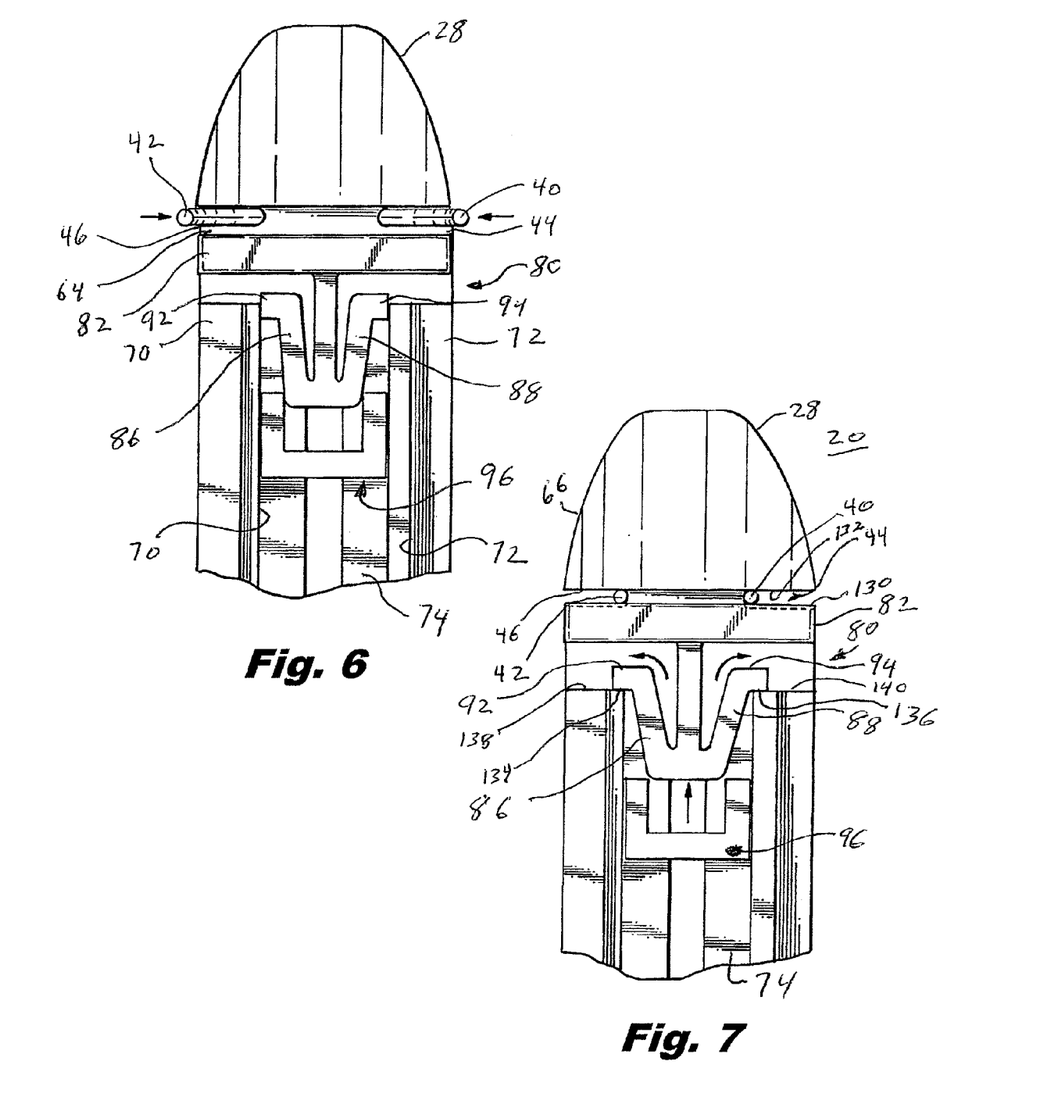
FIG. 6 is a top plan view of the distal end of the buttressed anvil assembly.
FIG. 7 is a top plan view of the distal end of the buttressed anvil assembly illustrating securement of the retention suture by the suture retention and release mechanism.

With reference to FIGS. 2, 3 and 6, thereafter, first and second ends 40 and 42 of retention component 36 are wrapped or passed through respective clearance tracks 44 and 46, formed in anvil member 28, until first and second ends 40 and 42 of retention component 36 are fully seated within clearance tracks 44 and 46. As noted herein above, clearance tracks 44 and 46 are dimensioned to loosely receive first and second ends 40 and 42 of retention component 36 without any pinching or cinching of first and second ends 40 and 42 within clearance tracks 44 and 46.

Referring now to FIG. 7, in order to secure retention component 36 to anvil member 28 and, specifically, secure first and second ends 40 and 42 within anvil member 28, retention member 80 is manually advanced distally to move push plate 82 through pocket 64 towards head 66. Retention member 80 is advanced distally until distal face 130 of push plate 82 captures first and second ends 40 and 42 of retention component 36 against proximal face 132 of head 66. In this manner, retention component 36, and thus strip of buttress material 30, is secured to anvil member 28.

As noted here in above, tabs 92 and 94 are provided in order to lock retention member 80 in the distal position. As retention member 80 is moved distally within channel 74 and pocket 64, tabs 92 and 94 move out of channel 74 and into pocket 64. As tabs 92 and 94 move out of channel 74, flexible arms 86 and 88 are free to move from the constrained condition to an open or expanded condition moving tabs 92 and 94 outwardly within pocket 64 until proximal faces 134 and 136 of tabs 92 and 94 engage distal faces 138 and 140 of first and second side walls 70 and 72. In this position, retention member 80 is locked in a distal most position securing retention component 36 to anvil member 28. As noted here in above, prior to use, follower 96 remains in a proximal position within channel 74.

Figures 8, 9:
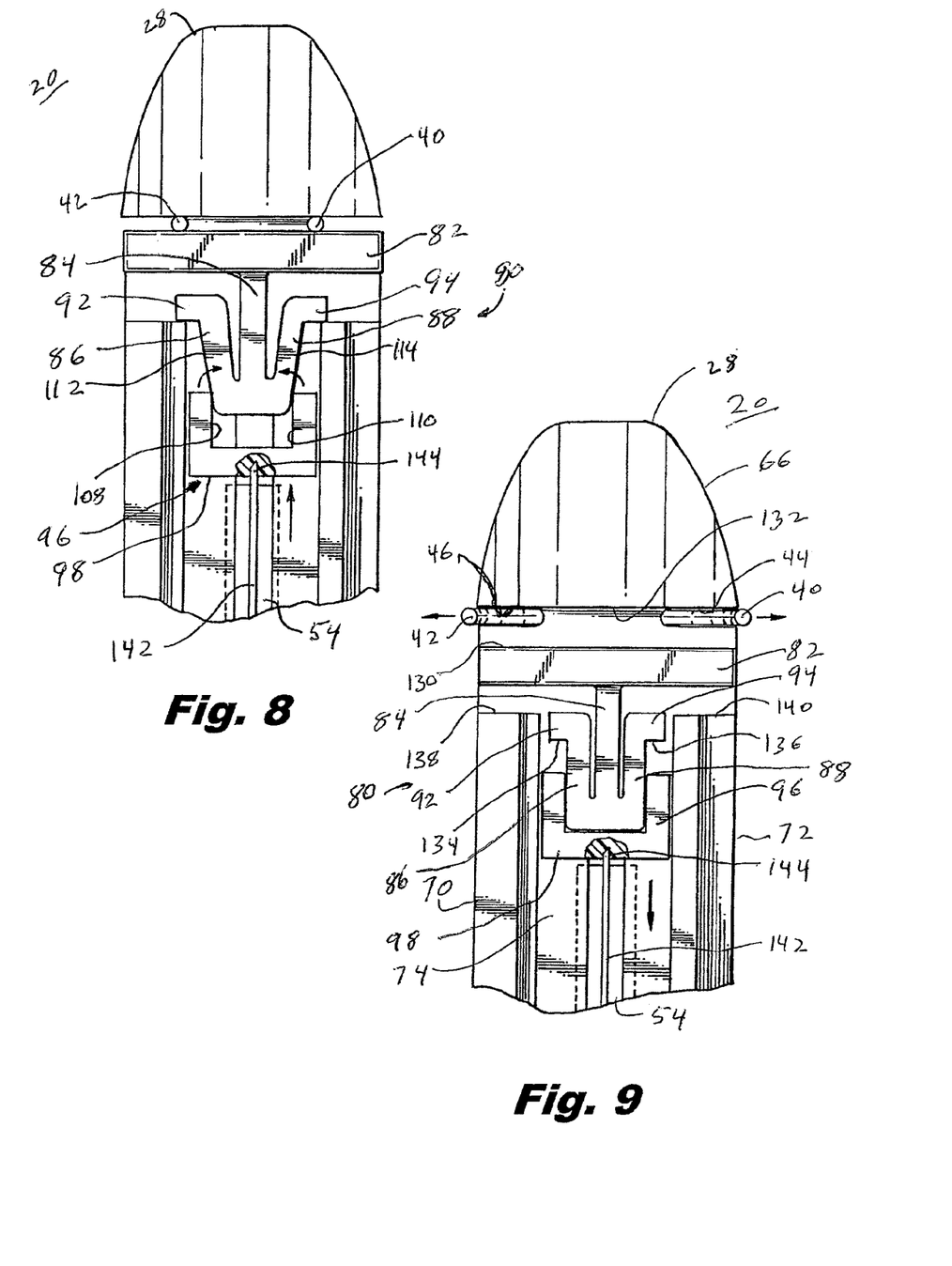
FIG. 8 is a top plan view of the distal end of the buttressed anvil assembly illustrating initial release of the suture retention and release mechanism.
FIG. 9 is a top plan view of the distal end of the buttressed anvil assembly illustrating release of the retention suture.

Referring now to FIGS. 1, 8 and 9, the use of surgical instrument 10 and, in particular, buttressed anvil assembly 20, will now be described. With reference to FIG. 1, in an initial position, buttressed anvil assembly 20 is in a spaced apart condition from staple cartridge 22. Thereafter, while not specifically shown, surgical instrument 10 is manipulated to position staple cartridge 22 and buttressed anvil assembly 20 about tissue to be stapled. Trigger 24 is then actuated to move buttressed anvil assembly 22 from the open positioned spaced from staple cartridge 22 to the closed position in close cooperatives alignment with staple cartridge 22 and about the tissue. Further actuation of trigger 24 serves to eject staples from staple cartridge 22 through the tissue and strip of buttress material 30 and into staple clenching pockets 52 formed in anvil face 34 (FIG. 3). As staples are ejected into clenching pockets 52, a knife blade passes through knife slot 54 to sever the stapled tissue and strip of buttress material 30. As noted herein above, in the event that strip of buttress material 30 is not completely severed by the knife blade, a perforation line may be formed in distal end 58 of strip of buttress material 30 to allow strip of buttress material to fully separate into two halves.

Referring now to FIG. 8, as a knife blade, such as, for example, knife blade 142 moves distally within channel 54, a distal end 144 of knife blade 142 engages backspan 98 of follower 96. Distal movement of knife blade 142 forces follower 96 distally within channel 74 causing follower 96 to engage retention member 80. Specifically, as follower 96 moves distally, inner surfaces 108 and 110 of respective legs 100 and 102 engage outer surfaces 112 and 114 of flexible arms 86 and 88 of retention member 80. This causes flexible arms 86 and 88 to be forced inwardly toward the constrained condition pulling tabs 92 and 94 inwardly toward bar 84.

Referring now to FIG. 9, as follower 96 is fully advanced over legs 86 and 88 of retention member 80, tabs 92 and 94 are moved to a fully inward position disengaging proximal faces 134 and 136 of tabs 92 and 94 from distal faces 138 and 140 of side walls 70 and 72. This "unlocks" retention member 80, allowing the retention member to move away from its locked position, releasing the pressure of push plate 82 from first and second ends 40 and 42 of retention component 36. In this condition, first and second ends 40 and 42 can be pulled free of clearance tracks 44 and 46 to thereby release retention component 36 and a strip of buttress material 30 from anvil member 28.

In the situation wherein follower 96 is formed of a penetrable material such as, for example, a plastic material, distal end 144 of knife blade 142 will penetrate backspan 98 of follower 96. Proximal movement of knife blade 142 through knife channel 54 draws follower 96, and thus retention member 80, proximally pulling push plate 82 further away from first and second ends 40 and 42 of retention suture 36 to thereby further release retention component 36 from anvil member 28. In this manner, retention and release mechanism 60 functions to initially secure retention suture 36, and thus strip of buttress material 30, to anvil member 28 and, upon subsequent operation of surgical instrument 10, allow retention suture 36 and strip of buttress material 30 to be released from anvil member 28.

It will be understood that various modifications may be made to the embodiments disclosed herein. For example, as noted herein above, only one end of the retention component need be free to be released from the anvil member while the opposing end of the retention component or suture may be secured to the anvil member, such as by use of adhesive or retention in a cinch slot. Further, the disclosed retention member may utilize only one flexible leg to secure the retention member in a distal position. Additionally, other means of engaging the knife blade with the disclosed follower can be provided such as, for example, magnetic, adhesives, etc. to allow the knife blade to move the follower to a proximal position within the disclosed anvil member. Further, in certain embodiments a separate activation bar or pusher is provided to release retention member 80 discussed above in connection with FIGS. 1, 8 and 9, independently from the actuation of the surgical stapling instrument 10. Therefore, the above description should not be construed as limiting, but merely as exemplifications of particular embodiments. Those skilled in the art will envision other modifications within the scope and spirit of the claims appended hereto.

The invention claimed is:

1. A surgical instrument comprising:
 a handle having a movable part mounted to the handle;
 an elongate tubular member extending distally from the handle member;
 an end effector assembly mounted on a distal end of the elongate tubular member, the end effector assembly including a first member having an underside and a top side, the underside having a face;
 a strip of buttress material positioned against the face;
 a retention component having a backspan and first and second ends extending from the backspan, the backspan being positioned across the strip of buttress material and the first end extends from the underside to the top side of the first member; and
 a retention member movably mounted on the top side of the first member, wherein the first end of the retention component is releasably secured between a distal face of the retention member and a proximal face of the first member.

2. The surgical instrument as recited in claim 1, wherein the top side of the first member includes an head and a pocket located proximal to the head.

3. The surgical instrument as recited in claim 2, wherein the retention member is movably mounted in the pocket and the first end of the retention component is releasably secured between a proximal face of the head and the distal face of the retention member.

4. The surgical instrument as recited in claim 3, wherein the retention member includes a push plate having a distal face, the first end of the retention component being releasably secured between the distal face of the push plate and the proximal face of the head.

5. The surgical instrument as recited in claim 4, wherein the first member has a pair of sidewalls defining a channel, each sidewall having a distal face, and the retention member includes a tab movable between the channel and the pocket such that a proximal face of the tab engages a distal face of the sidewall when the tab is in the pocket.

6. The surgical instrument as recited in claim 5, wherein the retention member includes a flexible leg, the tab being located on a distal end of the flexible leg.

7. The surgical instrument as recited in claim 6, wherein the retention member includes a bar extending from the push plate to a proximal end of the flexible leg such that the tab is within the channel when the retention member is in a proximal position and is in engagement with the distal face of the side wall when the retention member is in a distal position to lock the push plate into engagement with the first end of the retention component.

8. The surgical instrument as recited in claim 7, wherein the flexible leg is in a constrained condition in the channel and in an expanded condition when the tab is distal of the distal face of the side wall.

9. The surgical instrument as recited in claim 8, wherein the retention and release mechanism further includes a follower movable within the channel, the follower being engageable with the flexible leg to move the flexible leg between the constrained and expanded conditions.

10. The surgical instrument as recited in claim 6, wherein the retention member includes a second flexible leg affixed to the proximal end of the bar, the second flexible leg including a tab engageable with one of the distal faces of the sidewalls.

11. The surgical instrument as recited in claim 3, wherein the anvil member includes a clearance track such that the first end of the retention component passes from the underside of the first member to the top side of the first member through the clearance track.

12. The surgical instrument as recited in claim 11, wherein the clearance track passes through the pocket.

13. The surgical instrument as recited in claim 11, wherein the first member has a second clearance track such that the second end of the retention component passes from the underside of the first member to the top side of the first member through the second clearance track.

14. The surgical instrument as recited in claim 1, wherein the strip of buttress material includes first and second cutouts for passage of the first and second ends of the retention component.

15. The surgical instrument as recited in claim 14, wherein the movable part is operable to move the retention member from a first position securing the retention component between a distal face of the retention member and a proximal face of the first member to a second position allowing the retention member to move away from the first and second ends of the retention component.

16. The surgical instrument as recited in claim 1, wherein the first member is an anvil member and further comprising a second member, the second member being a surgical stapling cartridge.

17. The surgical instrument as recited in claim 16, wherein the retention member has a locked position, the retention member securing the retention component in the locked position.

18. The surgical instrument as recited in claim 17, wherein the retention member has at least one tab for maintaining the retention member in the locked position.

19. The surgical instrument as recited in claim 18, further comprising a follower for moving the at least one tab, allowing movement of the retention member away from the locked position.

\* \* \* \* \*